(12) United States Patent
Han et al.

(10) Patent No.: US 8,986,644 B2
(45) Date of Patent: Mar. 24, 2015

(54) METHOD FOR PREPARATION OF HIGH PURITY, CRYSTALLINE COBALT NITRATE FROM SPENT COBALT/SILICA CATALYST

(71) Applicant: Wuhan Kaidi Engineering Technology Research Institute Co., Ltd., Wuhan (CN)

(72) Inventors: Yiming Han, Wuhan (CN); Qianqian Liu, Wuhan (CN); Bo Lai, Wuhan (CN); Li Xu, Wuhan (CN); Dechen Song, Wuhan (CN)

(73) Assignee: Wuhan Kaidi Engineering Technology Research Institute Co., Ltd., Wuhan (CN)

( * ) Notice: Subject to any disclaimer, the term of this patent is extended or adjusted under 35 U.S.C. 154(b) by 0 days.

(21) Appl. No.: 14/477,909

(22) Filed: Sep. 5, 2014

(65) Prior Publication Data
US 2014/0377153 A1    Dec. 25, 2014

Related U.S. Application Data

(63) Continuation-in-part of application No. PCT/CN2013/072109, filed on Mar. 4, 2013.

(51) Int. Cl.
  *C22B 3/00*    (2006.01)
  *C22B 3/32*    (2006.01)

(52) U.S. Cl.
  CPC ........... *C22B 23/0438* (2013.01); *C22B 3/0025* (2013.01)

USPC ............... 423/395; 423/326; 423/594.5

(58) Field of Classification Search
  CPC .................. C01G 51/00; C01G 51/04
  USPC .......................................... 423/395
  See application file for complete search history.

(56) References Cited

FOREIGN PATENT DOCUMENTS

CN        101700913 A    *    5/2010

* cited by examiner

*Primary Examiner* — Melissa Swain
(74) *Attorney, Agent, or Firm* — Matthias Scholl P.C.; Matthias Scholl

(57) ABSTRACT

A method for preparing crystalline cobalt nitrate. The method includes: 1) calcining a spent $Co/SiO_2$ catalyst, cooling the calcined material to room temperature, and grinding it to yield a powder; 2) heating the powder in a fluidized bed reactor; 3) adding the heated powder into excess dilute nitric acid solution and filtering to obtain a cobalt nitrate solution; 4) adjusting the pH value of the cobalt nitrate solution to 1.5, adding a preheated oxalic acid solution, adjusting a pH value of the resulting solution to 1.5, immediately filtering the resulting solution to yield a precipitate of cobalt oxalate, washing the precipitate of cobalt oxalate to yield a neutral filtrate; 5) drying the precipitate and calcining to yield cobalt oxide; 6) dissolving the cobalt oxide in nitric acid to yield a second cobalt nitrate solution; and 7) evaporating the second cobalt nitrate solution to obtain crystalline cobalt nitrate.

9 Claims, No Drawings

METHOD FOR PREPARATION OF HIGH PURITY, CRYSTALLINE COBALT NITRATE FROM SPENT COBALT/SILICA CATALYST

CROSS-REFERENCE TO RELATED APPLICATIONS

This application is a continuation-in-part of International Patent Application No. PCT/CN2013/072109 with an international filing date of Mar. 4, 2013, designating the United States, now pending, and further claims priority benefits to Chinese Patent Application No. 201210055799.5 filed Mar. 5, 2012. The contents of all of the aforementioned applications, including any intervening amendments thereto, are incorporated herein by reference. Inquiries from the public to applicants or assignees concerning this document or the related applications should be directed to: Matthias Scholl P. C., Attn.: Dr. Matthias Scholl Esq., 245 First Street, 18th Floor, Cambridge, Mass. 02142.

BACKGROUND OF THE INVENTION

1. Field of the Invention

The invention relates to a method for preparation of high purity, crystalline cobalt nitrate from spent $Co/SiO_2$ catalyst.

2. Description of the Related Art

Cobalt is a rare metal. Silica supported cobalt-based $Co/SiO_2$ catalyst is highly active in catalytic hydrogenation. Recycling cobalt from a cobalt-based spent catalyst decreases environmental pollution and improves the utilization of the cobalt resources.

A typical method for recycling cobalt includes precipitating cobalt ions to yield $Co(OH)_2$, and dissolving $Co(OH)_2$ in nitric acid to obtain $Co(NO_3)_2 \cdot 6H_2O$. However, the purity of $Co(NO_3)_2 \cdot 6H_2O$ obtained by this method is less than 98%. In addition, the fine granules of intermediate CoS produced during the recycling process are difficult to filter, which causes cobalt loss during filtration and leads to a low recovery rate of cobalt.

SUMMARY OF THE INVENTION

In view of the above-described problems, it is one objective of the invention to provide a method for preparing high purity, crystalline cobalt nitrate from a spent catalyst of $Co/SiO_2$. The method features a high recovery rate and high product purity.

To achieve the above objective, in accordance with one embodiment of the invention, there is provided a method for preparing crystalline cobalt nitrate from a spent catalyst of $Co/SiO_2$, the method comprises the following steps:

1) calcining a spent catalyst of $Co/SiO_2$ in the presence of air for between 3 and 6 hours at a temperature of between 350 and 500° C., cooling to room temperature, and grinding the spent catalyst of $Co/SiO_2$ to yield a powder;

2) introducing the powder to a fluidized bed reactor, heating the powder for between 8 and 12 hours in the presence of a mixed gas of $H_2$ and $N_2$, a volume ratio of $H_2$ to $N_2$ in the mixed gas being between 1:1 and 4:1;

3) adding the heated powder into excess dilute nitric acid solution and filtering to obtain a cobalt nitrate solution;

4) adjusting a pH value of the cobalt nitrate solution to 1.5 using an alkali solution, adding a preheated oxalic acid solution having a temperature of between 25 and 80° C. and a pH value of 1.5 to the cobalt nitrate solution in a water bath of between 25 and 80° C., adjusting a pH value of a resulting solution to 1.5 using a dilute alkali solution, immediately filtering the resulting solution to yield a precipitate of cobalt oxalate, washing the precipitate of cobalt oxalate using deionized water to yield a neutral filtrate; in this step, the mole number of oxalic acid in the oxalic acid solution is controlled to be between 2 and 3 times a mole number of cobalt in the cobalt nitrate solution;

5) drying the precipitate of cobalt oxalate and calcining for between 4 and 8 hours at a temperature of between 550 and 650° C. to yield cobalt oxide;

6) dissolving the cobalt oxide with a dilute nitric acid solution to yield a second cobalt nitrate solution; and 7) evaporating and crystallizing the second cobalt nitrate solution to yield crystalline $Co(NO_3)_2 \cdot 6H_2O$.

In a class of this embodiment, in step 2), a space velocity of the mixed gas is between 1000 and 4000 $h^{-1}$, a pressure within the fluidized bed reactor is between 0.1 and 1 MPa, and a reaction temperature is between 350 and 750° C.

In a class of this embodiment, in step 3), the dilute nitric acid solution has a concentration of from 1 to 3 mol/L.

In a class of this embodiment, in step 6), the dilute nitric acid solution has a concentration of from 1 to 3 mol/L.

In a class of this embodiment, in step 4), the water bath has a temperature of 70° C., the oxalic acid solution is preheated to 70° C., and the deionized water is preheated to 70° C.

Advantages of the present disclosure are summarized as follows. The invention employs a spent catalyst of $Co/SiO_2$ from Fischer-Tropsch process to prepare a high purity, crystalline cobalt nitrate. Heavy hydrocarbons on the surface of the catalyst are removed through aerobic calcination. The metal oxide in the spent catalyst is reduced by a reducing mixed gas comprising more than 50 vol. % of hydrogen to yield cobalt. The reduction product is dissolved in excess dilute nitric acid to yield the cobalt nitrate solution, which is allowed to react with an oxalic acid solution to produce a precipitate of cobalt oxalate. The oxalic acid solution is added in excess so as to facilitate the precipitation of cobalt thereby improving the conversion of cobalt. In addition, the pH value is controlled at about 1.5 to ensure complete precipitation of cobalt in the form of cobalt oxalate. The temperature is controlled at between 25 and 80° C., particularly at 70° C., because a lower temperature leads to tiny granules of cobalt oxalate which causes a great loss of cobalt in the next filtering and washing. In the process of precipitating cobalt oxalate, the released hydrogen ions decrease the pH value of the mixture. Therefore, in order to achieve complete precipitation of cobalt, the pH value at the reaction end should be adjusted to 1.5. Thereafter, the cobalt oxalate is decomposed at a high temperature to yield cobalt oxide, and the latter is added to dilute nitric acid to yield a solution of cobalt nitrate. The solution is evaporated and crystallized to yield high purity, crystalline $Co(NO_3)_2 \cdot 6H_2O$.

The process conditions are strictly controlled so that the resulting product has a high recovery rate and high purity, and can be directly used for the industrial applications. The method of the present disclosure has simple operation, short flow path, and low requirements on devices and process condition, and thus is suitable for large-scale applications.

DETAILED DESCRIPTION OF THE EMBODIMENTS

For further illustrating the invention, experiments detailing a method for preparing crystalline cobalt nitrate from a spent catalyst of $Co/SiO_2$ are described below. It should be noted that the following examples are intended to describe and not to limit the invention.

Example 1

1) 20.01 g of a spent catalyst of $Co/SiO_2$ comprising 12.1 wt. % of cobalt was collected. The spent catalyst was added to a muffle furnace, air was charged, and the temperature of the muffle furnace was increased from room temperature to 350° C. and maintained at 350° C. for 6 hours to remove heavy hydrocarbons from the surface of the catalyst. The muffle furnace was cooled to room temperature and a resulting product was uniformly ground to yield a powder.

2) The powder was introduced to a fluidized bed reactor, and heated in the presence of a mixed gas of $H_2$ and $N_2$ (a volume ratio of $H_2$ to $N_2$ in the mixed gas was 1:1) at 400° C. and 1 MPa for 10 hours, and the space velocity of the mixed gas was 4000 $h^{-1}$.

3) The heated powder was added to 200 mL of a dilute nitric acid solution having a concentration of 3 mol/L. The mixture was stirred, and filtered to collect a filtrate which was a cobalt nitrate solution.

4) The pH value of the cobalt nitrate solution was adjusted to 1.5 by saturated NaOH solution. 12.95 g of oxalic acid solid ($H_2C_2O_4.2H_2O$) was dissolved in deionized water to obtain an oxalic acid solution, and the pH value thereof was adjusted to 1.5 using 1 wt. % of NaOH solution. The oxalic acid solution was preheated to 70° C., added dropwise (0.01 mL/s) to the cobalt nitrate solution in a water bath of 70° C., and stirred for 15 min. The pH value of the resulting solution was adjusted to 1.5 using 5 wt. % NaOH solution, and the solution was filtered immediately to yield a precipitate of $CoC_2O_4$. The precipitate of $CoC_2O_4$ was washed with deionized water (70° C.) to yield a neutral filtrate.

5) The precipitate of $CoC_2O_4$ was dried and calcined in a muffle furnace at 550° C. for 5 hours to yield cobalt oxide ($Co_2O_3$).

6) The cobalt oxide was dissolved in 3 mol/L nitric acid solution to yield a second cobalt nitrate solution.

7) The second cobalt nitrate solution was evaporated in a 70° C. water bath while crystalline films constantly formed on the surface of the solution were collected. The crystalline films were dried to a constant weight to yield 11.57 g of $Co(NO_3)_2.6H_2O$.

According to the measurement method provided in GBT 15898-1995, the purity of the product of $Co(NO_3)_2.6H_2O$ was 99.40%, and the recovery percent of cobalt in this example was 96.18%.

Example 2

1) 10.24 g of a spent catalyst of $Co/SiO_2$ comprising 18.36 wt. % of cobalt was collected. The spent catalyst was added to a muffle furnace, air was charged, and the temperature of the muffle furnace was increased from room temperature to 400° C. and maintained at 400° C. for 4 hours to remove heavy hydrocarbons from the surface of the catalyst. The muffle furnace was cooled to room temperature and a resulting product was uniformly ground to yield a powder.

2) The powder was introduced to a fluidized bed reactor, and heated in the presence of a mixed gas of $H_2$ and $N_2$ (a volume ratio of $H_2$ to $N_2$ in the mixed gas was 3:1) at 750° C. and 0.5 MPa for 8 hours, and the space velocity of the mixed gas was 3000 $h^{-1}$.

3) The heated powder was added to 160 mL of a dilute nitric acid solution having a concentration of 2 mol/L. The mixture was stirred, and filtered to collect a filtrate which was a cobalt nitrate solution.

4) The pH value of the cobalt nitrate solution was adjusted to 1.5 by saturated NaOH solution. 10.05 g of oxalic acid solid ($H_2C_2O_4.2H_2O$) was dissolved in deionized water to obtain an oxalic acid solution, and the pH value thereof was adjusted to 1.5 using 1 wt. % of NaOH solution. The oxalic acid solution was preheated to 70° C., added dropwise (0.01 mL/s) to the cobalt nitrate solution in a water bath of 70° C., and stirred for 15 min. The pH value of the resulting solution was adjusted to 1.5 using 5 wt. % NaOH solution, and the solution was filtered immediately to yield a precipitate of $CoC_2O_4$. The precipitate of $CoC_2O_4$ was washed with deionized water (70° C.) to yield a neutral filtrate.

5) The precipitate of $CoC_2O_4$ was dried and calcined in a muffle furnace at 650° C. for 4 hours to yield cobalt oxide ($Co_2O_3$).

6) The cobalt oxide was dissolved in 3 mol/L nitric acid solution to yield a second cobalt nitrate solution.

7) The second cobalt nitrate solution was evaporated in a 70° C. water bath while crystalline films constantly formed on the surface of the solution were collected. The crystalline films were dried to a constant weight to yield 9.04 g of $Co(NO_3)_2.6H_2O$.

According to the measurement method provided in GBT 15898-1995, the purity of the product of $Co(NO_3)_2.6H_2O$ was 99.57%, and the recovery percent of cobalt in this example was 96.94%.

Example 3

1) 15.62 g of a spent catalyst of $Co/SiO_2$ comprising 22.64 wt. % of cobalt was collected. The spent catalyst was added to a muffle furnace, air was charged, and the temperature of the muffle furnace was increased from room temperature to 500° C. and maintained at 500° C. for 3 hours to remove heavy hydrocarbons from the surface of the catalyst. The muffle furnace was cooled to room temperature and a resulting product was uniformly ground to yield a powder.

2) The powder was introduced to a fluidized bed reactor, and heated in the presence of a mixed gas of $H_2$ and $N_2$ (a volume ratio of $H_2$ to $N_2$ in the mixed gas was 4:1) at 600° C. and 0.1 MPa for 12 hours, and the space velocity of the mixed gas was 1000 $h^{-1}$.

3) The heated powder was added to 300 mL of a dilute nitric acid solution having a concentration of 1 mol/L. The mixture was stirred, and filtered to collect a filtrate which was a cobalt nitrate solution.

4) The pH value of the cobalt nitrate solution was adjusted to 1.5 by saturated NaOH solution. 18.91 g of oxalic acid solid ($H_2C_2O_4.2H_2O$) was dissolved in deionized water to obtain an oxalic acid solution, and the pH value thereof was adjusted to 1.5 using 1 wt. % of NaOH solution. The oxalic acid solution was preheated to 70° C., added dropwise (0.01 mL/s) to the cobalt nitrate solution in a water bath of 70° C., and stirred for 15 min. The pH value of the resulting solution was adjusted to 1.5 using 5 wt. % NaOH solution, and the solution was filtered immediately to yield a precipitate of $CoC_2O_4$. The precipitate of $CoC_2O_4$ was washed with deionized water (70° C.) to yield a neutral filtrate.

5) The precipitate of $CoC_2O_4$ was dried and calcined in a muffle furnace at 600° C. for 8 hours to yield cobalt oxide ($Co_2O_3$).

6) The cobalt oxide was dissolved in 1 mol/L nitric acid solution to yield a second cobalt nitrate solution.

7) The second cobalt nitrate solution was evaporated in a 70° C. water bath while crystalline films constantly formed on the surface of the solution were collected. The crystalline films were dried to a constant weight to yield 16.94 g of $Co(NO_3)_2.6H_2O$.

According to the measurement method provided in GBT 15898-1995, the purity of the product of $Co(NO_3)_2 \cdot 6H_2O$ was 99.63%, and the recovery percent of cobalt in this example was 96.64%.

Example 4

1) 15.62 g of a spent catalyst of $Co/SiO_2$ comprising 22.64 wt. % of cobalt was collected. The spent catalyst was added to a muffle furnace, air was charged, and the temperature of the muffle furnace was increased from room temperature to 450° C. and maintained at 450° C. for 5 hours to remove heavy hydrocarbons from the surface of the catalyst. The muffle furnace was cooled to room temperature and a resulting product was uniformly ground to yield a powder.

2) The powder was introduced to a fluidized bed reactor, and heated in the presence of a mixed gas of $H_2$ and $N_2$ (a volume ratio of $H_2$ to $N_2$ in the mixed gas was 3:1) at 350° C. and 0.3 MPa for 10 hours, and the space velocity of the mixed gas was 3000 $h^{-1}$.

3) The heated powder was added to 300 mL of a dilute nitric acid solution having a concentration of 1 mol/L. The mixture was stirred, and filtered to collect a filtrate which was a cobalt nitrate solution.

4) The pH value of the cobalt nitrate solution was adjusted to 1.5 by saturated NaOH solution. 22.12 g of oxalic acid solid ($H_2C_2O_4 \cdot 2H_2O$) was dissolved in deionized water to obtain an oxalic acid solution, and the pH value thereof was adjusted to 1.5 using 1 wt. % of NaOH solution. The oxalic acid solution was preheated to 80° C., added dropwise (0.01 mL/s) to the cobalt nitrate solution in a water bath of 80° C., and stirred for 15 min. The pH value of the resulting solution was adjusted to 1.5 using 5 wt. % NaOH solution, and the solution was filtered immediately to yield a precipitate of $CoC_2O_4$. The precipitate of $CoC_2O_4$ was washed with deionized water (70° C.) to yield a neutral filtrate.

5) The precipitate of $CoC_2O_4$ was dried and calcined in a muffle furnace at 600° C. for 6 hours to yield cobalt oxide ($Co_2O_3$).

6) The cobalt oxide was dissolved in 1 mol/L nitric acid solution to yield a second cobalt nitrate solution.

7) The second cobalt nitrate solution was evaporated in a 70° C. water bath while crystalline films constantly formed on the surface of the solution were collected. The crystalline films were dried to a constant weight to yield 17.32 g of $Co(NO_3)_2 \cdot 6H_2O$.

According to the measurement method provided in GBT 15898-1995, the purity of the product of $Co(NO_3)_2 \cdot 6H_2O$ was 99.55%, and the recovery percent of cobalt in this example was 97.04%.

Unless otherwise indicated, the numerical ranges involved in the invention include the end values.

While particular embodiments of the invention have been shown and described, it will be obvious to those skilled in the art that changes and modifications may be made without departing from the invention in its broader aspects, and therefore, the aim in the appended claims is to cover all such changes and modifications as fall within the true spirit and scope of the invention.

The invention claimed is:

1. A method for preparing crystalline cobalt nitrate from spent catalyst of $Co/SiO_2$, the method comprising:
   1) calcining a spent catalyst of $Co/SiO_2$ in the presence of air for between 3 and 6 hours at a temperature of between 350 and 500° C., cooling to room temperature, and grinding the spent catalyst of $Co/SiO_2$ to yield a powder;
   2) introducing the powder of 1) to a fluidized bed reactor, and heating the powder of 1) for between 8 and 12 hours in the presence of a mixed gas of $H_2$ and $N_2$ to obtain a heated powder, a volume ratio of $H_2$ to $N_2$ in the mixed gas being between 1:1 and 4:1;
   3) adding the heated powder of 2) into excess dilute nitric acid solution, and then filtering to obtain a first cobalt nitrate solution;
   4) adjusting a pH value of the first cobalt nitrate solution of 3) to 1.5 using an alkali solution, adding a preheated oxalic acid solution having a temperature of between 25 and 80° C. and a pH value of 1.5 to the first cobalt nitrate solution in a water bath of between 25 and 80° C. to obtain a resulting solution, adjusting a pH value of the resulting solution to 1.5 using a dilute alkali solution, immediately filtering the resulting solution to yield a precipitate of cobalt oxalate, and then washing the precipitate of cobalt oxalate using deionized water to yield a neutral filtrate, wherein a mole number of oxalic acid in the oxalic acid solution is controlled to be between 2 and 3 times a mole number of cobalt in the cobalt nitrate solution;
   5) drying the precipitate of cobalt oxalate of 4) to obtain a dried precipitate, and then calcining the dried precipitate for between 4 and 8 hours at a temperature of between 550 and 650° C. to yield cobalt oxide;
   6) dissolving the cobalt oxide of 5) with a dilute nitric acid solution to yield a second cobalt nitrate solution; and
   7) evaporating and crystallizing the second cobalt nitrate solution to yield crystalline $Co(NO_3)_2 \cdot 6H_2O$.

2. The method of claim 1, wherein in 2), a space velocity of the mixed gas is between 1000 and 4000 $h^{-1}$, a pressure of the fluidized bed reactor is between 0.1 and 1 MPa, and a reaction temperature is between 350 and 750° C.

3. The method of claim 2, wherein in 3), the dilute nitric acid solution has a concentration of from 1 to 3 mol/L.

4. The method of claim 2, wherein in 6), the dilute nitric acid solution has a concentration of from 1 to 3 mol/L.

5. The method of claim 3, wherein in 6), the dilute nitric acid solution has a concentration of from 1 to 3 mol/L.

6. The method of claim 2, wherein in 4), the water bath has a temperature of 70° C., the oxalic acid solution is preheated to 70° C., and the deionized water is preheated to 70° C.

7. The method of claim 3, wherein in 4), the water bath has a temperature of 70° C., the oxalic acid solution is preheated to 70° C., and the deionized water is preheated to 70° C.

8. The method of claim 4, wherein in 4), the water bath has a temperature of 70° C., the oxalic acid solution is preheated to 70° C., and the deionized water is preheated to 70° C.

9. The method of claim 5, wherein in 4), the water bath has a temperature of 70° C., the oxalic acid solution is preheated to 70° C., and the deionized water is preheated to 70° C.

* * * * *